US006661870B2

(12) United States Patent
Kapatoes et al.

(10) Patent No.: US 6,661,870 B2
(45) Date of Patent: Dec. 9, 2003

(54) FLUENCE ADJUSTMENT FOR IMPROVING DELIVERY TO VOXELS WITHOUT REOPTIMIZATION

(75) Inventors: Jeffrey M. Kapatoes, Madison, WI (US); Gustavo H. Olivera, Verona, WI (US); Paul J. Reckwerdt, Madison, WI (US); Thomas R. Mackie, Verona, WI (US); Kenneth J. Ruchala, Madison, WI (US)

(73) Assignee: TomoTherapy Incorporated, Madison, WI (US)

( * ) Notice: Subject to any disclaimer, the term of this patent is extended or adjusted under 35 U.S.C. 154(b) by 0 days.

(21) Appl. No.: 09/802,470

(22) Filed: Mar. 9, 2001

(65) Prior Publication Data

US 2002/0150207 A1 Oct. 17, 2002

(51) Int. Cl.[7] .................................................. A61N 5/10
(52) U.S. Cl. .......................................................... 378/65
(58) Field of Search ............................................ 378/65

(56) References Cited

U.S. PATENT DOCUMENTS

| | | |
|---|---|---|
| 5,317,616 A | 5/1994 | Swerdloff et al. |
| 5,351,280 A | 9/1994 | Swerdloff et al. |
| 5,394,452 A | 2/1995 | Swerdloff et al. |
| 5,442,675 A | 8/1995 | Swerdloff et al. |
| 5,528,650 A | 6/1996 | Swerdloff et al. |
| 5,548,627 A | 8/1996 | Swerdloff et al. |
| 5,625,663 A | 4/1997 | Swerdloff et al. |
| 5,647,663 A | 7/1997 | Holmes |
| 5,661,773 A * | 8/1997 | Swerdloff ..................... 378/65 |
| 5,673,300 A * | 9/1997 | Reckwerdt et al. ........... 378/65 |
| 5,724,400 A | 3/1998 | Swerdloff et al. |

* cited by examiner

Primary Examiner—Craig E. Church
(74) Attorney, Agent, or Firm—Godfrey & Kahn, S.C.; William K. Baxter

(57) ABSTRACT

A method of compensating for unexpected changes in the size, shape, and/or position of a patient in the delivery of radiation therapy. An image of a patient is used to prepare a treatment plan for the irradiation of a tumor or the like, shown in the image. A second image of a patient includes a visual representation of the tumor and sensitive structures wherein any combination of the size, shape, or position of the tumor or sensitive structures is different from any combination of the size, shape, or position of the visual representation of the tumor or sensitive structures in said first image. The radiation treatment is adjusted to more closely conform the treatment plan to the new size, shape, or position of the tumor as shown in said second image. This adjustment can occur before, during, or after the radiation delivery and can be used to define trade-offs that exist for the delivery. The trade-offs can be assessed and decisions made regarding which fluence adjustment strategy will be acceptable for treatment delivery.

17 Claims, 4 Drawing Sheets

FLUENCE ADJUSTMENT FOR IMPROVING DELIVERY TO VOXELS WITHOUT REOPTIMIZATION

FIELD OF THE INVENTION

This invention relates generally to the use of radiation therapy equipment for the treatment of tumors, or the like, and specifically to a method for modifying a prepared radiation treatment plan in response to a detected change in a tumor, or the like.

BACKGROUND OF THE INVENTION

Medical equipment for radiation therapy treats tumorous tissue with high energy radiation. The amount of radiation and its placement must be accurately controlled to ensure both that the tumor receives sufficient radiation to be destroyed, and that the damage to the surrounding and adjacent non-tumorous tissue is minimized.

In external beam radiation therapy, a radiation source external to the patient treats internal tumors. The external source is normally collimated to direct a beam only to the tumorous site. The source of high energy radiation may be x-rays, or electrons from linear accelerators in the range of 2–25 MeV, or gamma rays from highly focused radioisotopes such as a $Co^{60}$ source having an energy of 1.25 MeV.

Typically the tumor will be treated from several different angles with the intensity and shape of the beam adjusted appropriately. The purpose of using multiple beams, which converge on the site of the tumor, is to reduce the dose to areas of surrounding non-tumorous tissue. The angles at which the tumor is irradiated are selected to avoid angles which would result in irradiation of particularly sensitive structures near the tumor site. The angles and intensities of the beams for a particular tumor form a treatment plan for that tumor.

One highly accurate method of controlling the dose to a patient employs a radiation source that produces a fan beam composed of many individual rays whose intensity may be independently controlled. The fan beam orbits the patient within a plane illuminating a slice of the patient, while the intensity of each ray of the fan beam is modulated as a function of that angle. By properly selecting the beam intensities at different angles, complex regions within the slice may be accurately irradiated. U.S. Pat. No. 5,317,616, issued May 31, 1994, describes the construction of one such machine and one method of calculating the necessary beam intensities as a function of angle.

In order to take advantage of the improved accuracy in dose placement offered by such radiation therapy systems, the radiation treatment plan may be based on a computed tomography ("CT") image of the patient. As is known in the art, a CT image is produced by a mathematical reconstruction of many projection images obtained at different angles about the patient. In a typical fan beam CT acquisition, the projections are one-dimensional line images indicating the attenuation of the fan beam by a "slice" of the patient. After reconstruction of the two-dimensional tomographic image of the slice, the projection data, which by itself is unintelligible, is no longer used or accessed by the user.

Using the CT image, the radiologist views the tumorous area and determines the beam angles and intensities (identified with respect to the tumor image) which will be used to treat the tumor. In an automated system, such as that described in U.S. Pat. No. 5,317,616 issued to Swerdloff, and incorporated herein by reference, a computer program selects the beam angles and intensities after the physician identifies the tumorous region and nearby sensitive structures, and upper and lower dose limits for the treatment. The region of interest is represented by a 3-D array of voxels, as is known in the art.

Normally, the CT image of the patient is acquired substantially before the radiation treatment to allow time for the treatment plan to be prepared. As a result, the tumor or sensitive structures may have grown or otherwise deformed to a shape different from that when the CT image was first acquired. This may also be true in cases where the treatment occurs during a number of different treatment sessions over time.

SUMMARY OF THE INVENTION

The present invention provides a system and method for adjusting the original optimized intensity to address over or under dosage caused by growth, deformation or other changes in shape or position of a tumor or diseased tissue between the time of a planning CT image and radiotherapy. Generally, this is done by determining a dose for an image acquired just prior to radiation treatment, and comparing this dose distribution with the planned dose distribution to ascertain which voxels need a dosage adjustment.

In the rotational radiotherapy delivery system with which the present system and method are preferably employed, a series of steps are normally undertaken to deliver complete patient treatment. Those steps are:

1. image input;
2. planning;
3. optimized treatment planning;
4. patient positioning/registration;
5. delivery modification;
6. delivery;
7. delivery verification;
8. dose reconstruction; and
9. deformable dose registration.

The image input step consists of a clinician taking images of a patient, for example CT or MRI images, to establish a region of interest (e.g., a tumor and possibly a portion of the surrounding tissue) and regions at risk (i.e., sensitive organs or structures).

The planning step consists of a clinician formally designating the regions of interest and regions at risk (sensitive structures) in reliance on the images taken in the image input step. As part of the formal designation, the clinician determines the level of radiation each designated region should receive on the 2-D slices based upon the images previously obtained.

In the optimized treatment planning step, the system, based on the clinician's formal designation, calculates the appropriate pattern, position and intensity of the radiation beam to be delivered. This is often a very time intensive process, depending on the shape complexity of the region of interest. Typically, parts of the clinician's 2-D plan is not feasible due to shape constraints. This only becomes apparent after the system calculates what dosage each voxel in the region of interest will receive as a result of the clinician's plan. Thus, the clinician revises his or her plan according the calculated dosages, and determines what trade-offs to make for an optimal delivery. "Trade-offs" involve comparing the benefit of targeting a particular voxel with knowing it will damage tissue relating to another voxel. This is an iterative process that could take several hours. Re-optimization could occur immediately after this step by repeating what was done in the optimized treatment planning step, with new information. However, it involves the same iterative process, and is generally not practical to perform at this point.

In the patient positioning/registration step, the patient is carefully positioned on the table of the radiation therapy delivery system. Then, a helical scan is preferably taken to determine the precise location of the tumor and the patient's "offset" from his/her position: the difference between the patient's position during planning and the current position. This is preferably done in one of two ways: image fusion in which the radiotherapist superimposes the two images on a monitor, then manually or automatically adjust the planning image to get the best match; or registration in projection space in which the system calculates the best match using sinograms (the data from which a CT image is constructed), without reconstructing the images themselves. Re-optimization could occur after this step, but is generally too time consuming for practical purposes.

Delivery modification is the step in which the clinician compensates for changes in the patient's position or the location of the tumor. Using the offset calculated in the Patient Registration step, the system recalculates the delivery pattern based on the patient's displacement.

Delivery is the step in which the final delivery pattern is actually applied to the patient by the radiation therapy delivery system.

Delivery Verification uses a signal measured at an exit detector to verify the delivery by computing the energy fluence directed toward the patient. This information can be used to compare the current delivery with the planned delivery, as well as to reconstruct the dose. It also can shut down the unit if a delivery error is detected.

Dose Reconstruction uses the incident energy fluence delivered and a radiographic image that was obtained either before, after, or during the treatment, to compute the dose deposited to the patient ("reconstructed") and compared with the planned dose. This allows the physician to make an "apples-to-apples" comparison between the actual and planned dose, and if necessary adapt the treatment plan for the next session.

In the deformable dose registration step, the clinician obtains the reconstructed dose for a series of fractions. This permits the system to calculate a cumulative dose distribution. With this information, the clinician can study the treatment delivery, modify the treatment for future fractions, and analyze patient outcomes. If there are any changes in the patient anatomy from one fraction to the next or even within a fraction (called "deformations") they need to be taken into account when calculating the cumulative dose. Relying on anatomical, biomechanical, and region of interest information, deformable dose registration maps changes in the patient's anatomy between each fraction. Using this information, the reconstructed dose for each fraction will be mapped back to a reference image. These mapped doses can then be added to obtain an accurate cumulative dose measurement.

When the shape of the target has changed due to internal or external influences, the planned level of radiation that each designated region receives may no longer be optimal. For example, a tumor may have grown in size since the treatment was planned, or the position or shape of surrounding sensitive structures may have changed. If the planned therapy were administered without change, a portion of the tumor would be missed, thereby diminishing the effectiveness of the treatment. Alternatively, if the tumor has decreased in size, healthy tissue would be dosed with an unnecessary amount of radiation and tissue damage would occur. Rather than doing nothing to change the dosage, the energy fluence values can be adjusted prior to delivery so that underdosed target voxels receive more radiation, and overdosed region of risk voxels receive less radiation.

The fluence adjustment is made by comparing the planned dose distribution with a newly calculated dose distribution based on current images. A radiation oncologist or the like either approves the newly calculated dose, or ascertains what voxels need fluence adjustment prior to radiation delivery. In another embodiment of the present invention, fluence adjustments are made after the delivery step. This allows the physician to immediately reapply radiation to any new regions of interest so that the patient does not have to wait until the next treatment session, which could be many days later.

The method of the present invention can be used immediately after delivery modification, acquisition of a pretreatment CT image, dose reconstruction or optimization.

The foregoing and other objects and advantages of the invention will appear from the following description. In the description references made to the accompanying drawings which form a part hereof, and in which there is shown by way of illustration, several embodiments of the invention. Such embodiments do not necessarily represent the full scope of the invention, however, and reference must be made therefore to the claims herein for interpreting the scope of the invention.

DETAILED DESCRIPTION OF A PREFERRED EMBODIMENT

Figure 1:
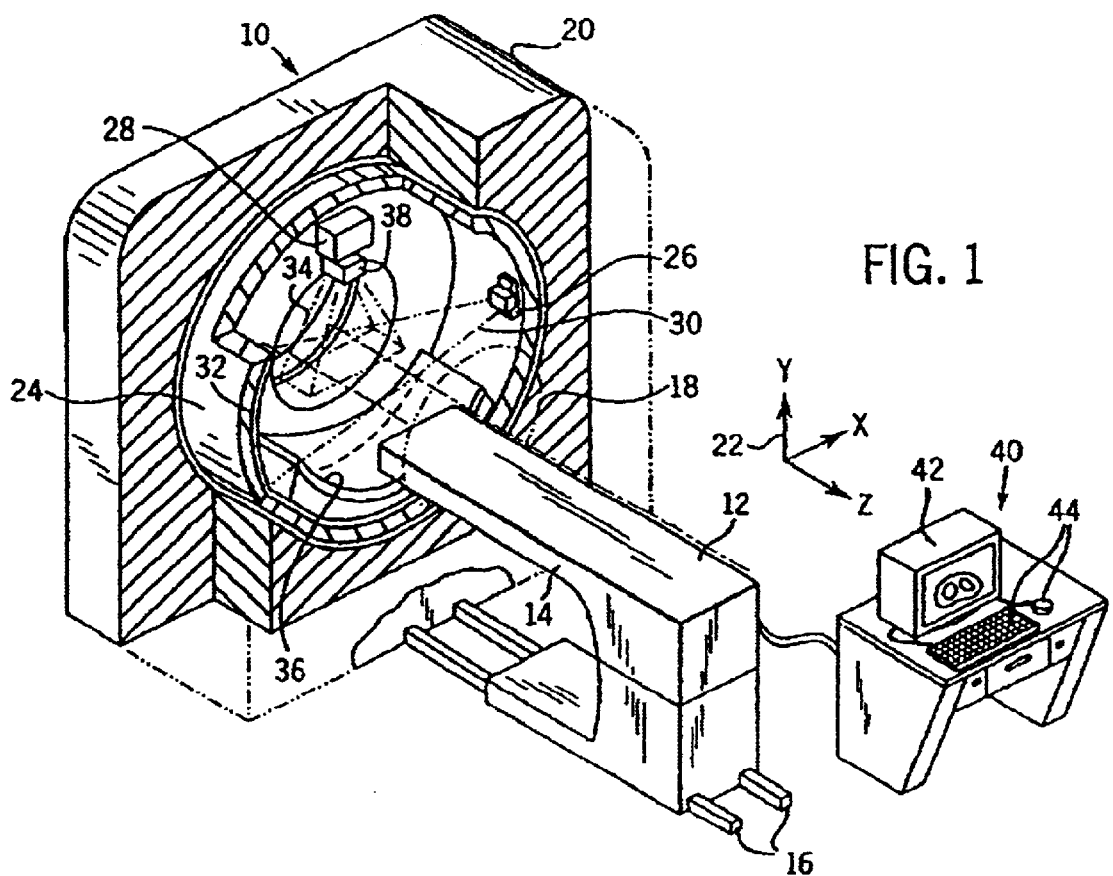
FIG. 1 is a perspective, cut-away view of a radiation therapy system providing for the acquisition of radiographic projections and for the generation of high energy radiation therapy beams and showing a patient table for supporting a patient thereon.

Referring now to FIG. 1, a radiation therapy machine 10, suitable for use with the present invention, includes a radiotranslucent table 12 having a cantilevered top 14. The table top 14 is received within a bore 18 of an annular housing 20 of the machine 10 with movement of the table 12 along tracks 16 extending along a z-axis of a Cartesian coordinate system 22. Table 12 also includes an internal track assembly and elevator (not shown) to allow adjustment of the top 14 in a lateral horizontal position (indicated by the x-axis of the coordinate system 22) and vertically (indicated by the y axis of the coordinate system 22). Motion in the x and y directions are limited by the diameter of the bore 18.

A rotating gantry 24, coaxial with the bore 18 and positioned within the housing 20, supports an x-ray source 26 and a high energy radiation source 28 on its inner surface.

The x-ray source 26 and a radiation source 28 rotate with the gantry 24 about a center of rotation 64 near the top of patient table 12 when the table top 14 is positioned within the bore 18.

The x-ray source 26 is collimated to produce a fan beam 30 lying generally within the x-y plane and crossing the bore 18 and thus the table top 14 when table top 14 is positioned within the bore 18. The fan beam 30 diverges about a central axis 31 whose angle is controlled by the position of the gantry 24.

After exiting the table top 14, the fan beam 30 is received by a linear array detector 32 positioned diametrically across from the x-ray source 26. Thus, the rotating gantry 24 permits fan beam radiographic projections of a patient on the table top 14 to be acquired at a variety of angles q about the patient during the treatment process.

The radiation source 28 is mounted so as to project a fan beam of high energy radiation 34, similar to the fan beam 30, but crossing fan beam 30 at right angles so as to be received on the other side of the gantry 24 by radiation detector and stop 36. Therefore, the x-ray can be taken of a region prior to application of radiation 34.

The radiation source 28 has a collimator 38 mounted in front of it to divide the fan beam of high energy radiation 34 into multiple adjacent rays whose intensity may be individually controlled to adjust the fluence. A collimator of this type is described in U.S. Pat. No. 5,317,616 assigned to the assignee of the present case and hereby incorporated by reference. The location of the radiation source 28 and x-ray source 26 are precisely characterized so that images obtained from the x-ray source 26 may be used to aim the radiation source 28.

A computer 40 having a display screen 42 and user entry mouse and keyboard 44 well known in the art is connected to the radiotherapy machine 10 to control motion of the table 12 and to coordinate operation of the gantry 24 together with the radiation source 28 and x-ray source 26 and to collect data from the linear array detector 32 during a scan of the patient according to methods well known in the art.

Figure 2:
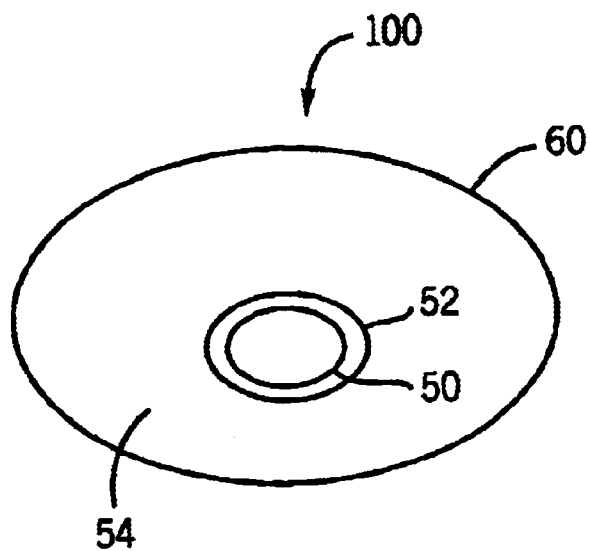
FIG. 2 is a schematic representation of a patient CT scan image showing a tumor.

A schematic treatment image 100 shown in FIG. 2 represents one "slice" of an image used to create a radiation treatment plan for a patient 60, typically determined during the optimized treatment planning step, described herein. FIG. 2 shows an abdominal tumor 50 or other tissue designated for radiation treatment. The full radiation treatment plan is prepared from a plurality of slices or images taken through the region of interest. A physician marks each separate image to indicate which areas receive a particular level of radiation, and the treatment plan is optimized as described previously. For example, if the physician wants to administer two levels of radiation intensities to the region of interest, the radiation treatment plan will direct beams of high intensity radiation to conform generally to the tumor volume corresponding to tumor 50 lying within the region of interest 52, while directing a low dose to the remaining region of interest 52 surrounding tumor 50.

Figure 3:
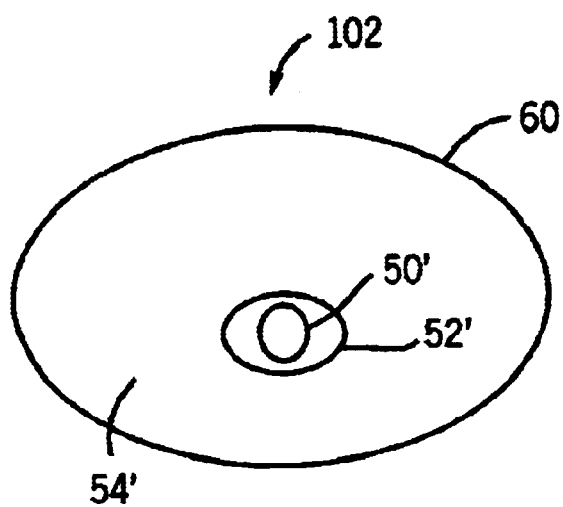
FIG. 3 is a schematic representation of a patient CT scan image in FIG. 2 showing a change in the tumor size.

At a later period, when radiation therapy is to begin, changes may have occurred to the target of patient 60. Thus, in one embodiment of the present invention, a confirmation image 102 is obtained prior to delivery, as shown by example in FIG. 3. Simply by comparing treatment image 100 to confirmation image 102, it can be seen that if the treatment plan were carried out according to a treatment image 100, the planned dose would not optimally treat the target defined by region of interest 52, which includes tumor 50, and/or may negatively affect the region at risk 54 surrounding the region of interest 52. In this particular example, tumor 50 has decreased in size to that seen as tumor 50' in FIG. 3. Likewise, the region of interest 50 has shrunk in size to that of region of interest 52', leaving a larger area at risk 54'.

The computer 40 is used to analyze the new information contained in confirmation image 102 by creating a new dose distribution. Specifically, it is the dose distribution that will result if the planned fluence is delivered without adjustment. New regions of interest are automatically prepared by computer or manually drawn based on the present anatomy embodied in confirmation image 102, and based upon the revised dose distribution and contours, the computer determines which voxels are receiving radiation less than or greater than the limits previously set by the physician during the optimization step. With this new information, the radiation oncologist or other trained person can choose to accept or reject the adjustments that have been made. In the case of rejection, the radiation oncologist changes the dose thresholds for any number of regions of interest and then applies the method of this invention until he or she decides that the dose distribution is acceptable. The decision regarding what is acceptable will depend upon the physician who will individually deal with the sometimes readily apparent trade-offs associated with a delivery. Trade-offs become apparent to the person making the adjustments because under such circumstances, the dose distribution that results from the original set of dose thresholds contains unfavorable characteristics that can only be remedied if a different strategy is explored.

Figure 4:
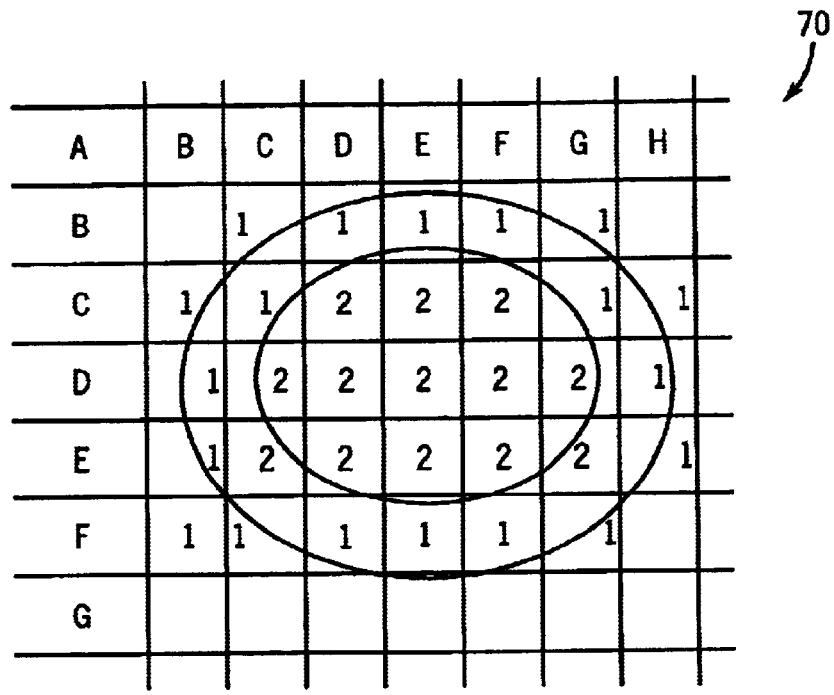
FIG. 4 is an enlarged view of the a voxel grid located in the region of interest in FIG. 2.
Figure 5:
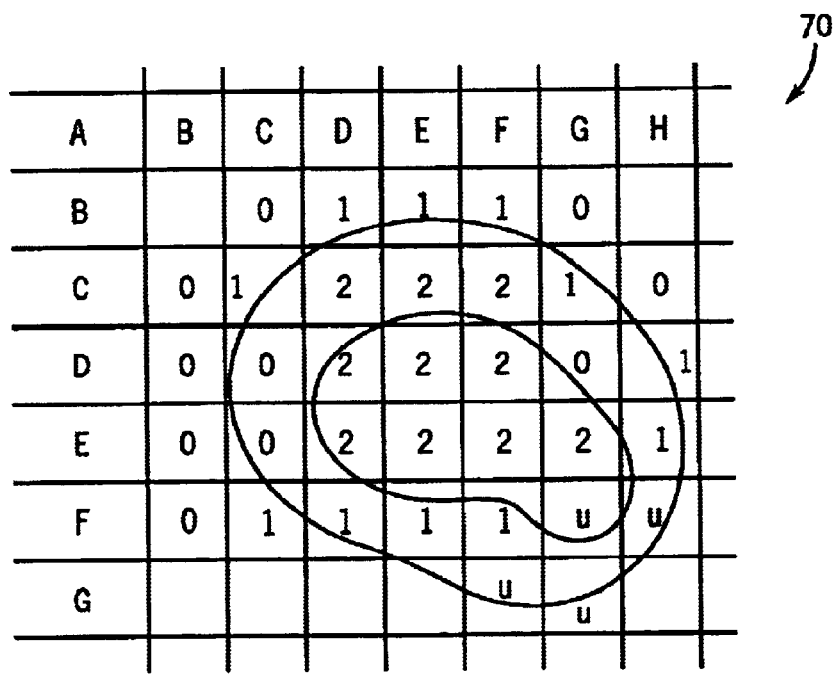
FIG. 5 is an enlarged view of a voxel grid located in the region of interest in FIG. 3.
Figure 6:
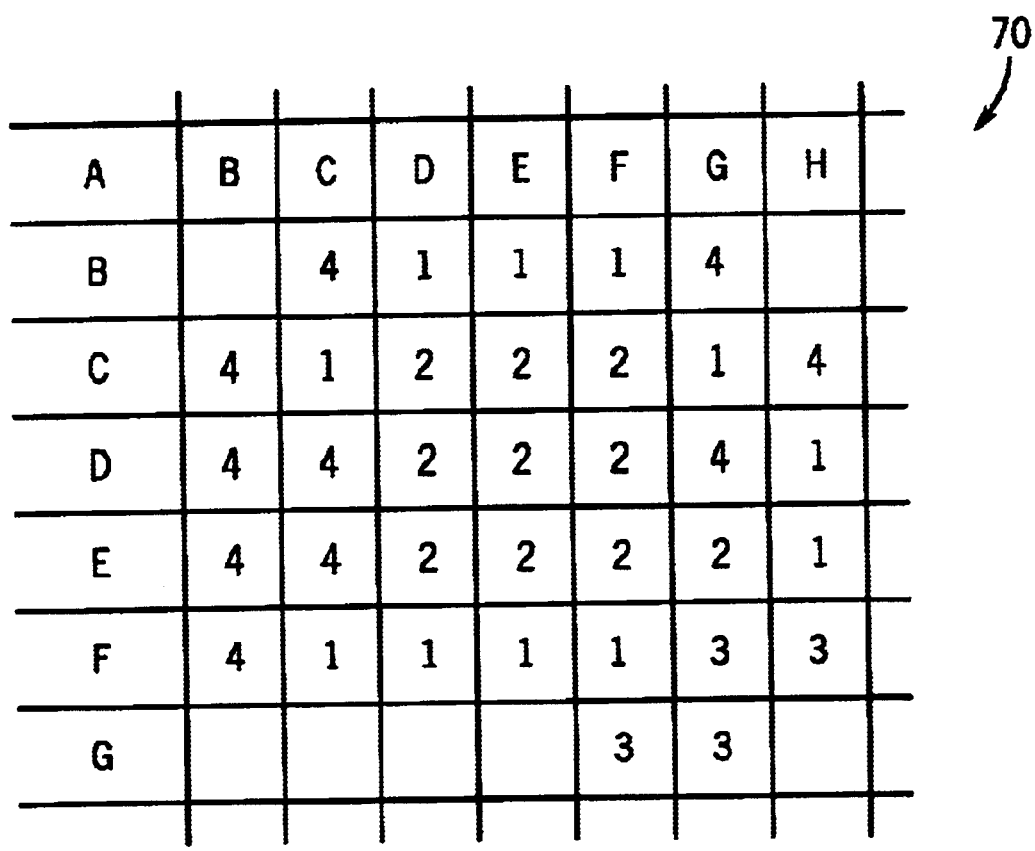
FIG. 6 is a voxel grid wherein fluence adjustments have been made in accordance with one embodiment of the present invention.

Specifically, FIG. 4 shows an exemplar voxel grid 70 in the region of interest, with the prescribed dose distribution indicated as "1" or "2," 1 being a lower dose than 2. FIG. 5 shows how a change in tumor shape leads to overdosed voxels designated as "O," and underdosed voxels designated as "U," if the initial treatment plan is applied. The dose distribution that results after fluence adjustment is represented in FIG. 6. An upwards adjustment in radiation dosage is represented as a "3," and a downwards adjustment as "4." This may not be the same dose that would be prescribed had the physician fully re-optimized the treatment plan based on the interative and time consuming optimization process as previously described, but it mitigates damage due to overdosing, and in cases where the tumor has changed shape or become enlarged, increases the effectiveness of the radiation therapy session by applying more radiation to otherwise underdosed voxels. The trade-offs can be quickly assessed and decisions made regarding which fluence adjustment strategy will be acceptable for treatment delivery without re-optimization.

The method of the present invention uses treatment information such as dose differences between the compared dose distributions, dose per energy fluence, radiological pathlength, beam importance, TERMA, TERMA per energy fluence etc. to generate plan modifications in order to correct the dose applied to each voxel in the voxel array. Preferably, the required change in dose is translated into a modification in TERMA for each voxel. This TERMA change is divided among the pencil beams that contribute to the voxel. The requested change in TERMA for each pencil beam is converted into an adjustment in their incident energy fluence. Various weighting strategies can be used in deciding which pencil beams will be used more heavily in others, including but not limited to, radiological pathlength traversed by the beam, volume of each type of structure encountered by the beam, mass of each type of structure encountered by the beam, etc. The actual fluence adjustment is done on the original planned intensity pattern, which is ultimately performed by the computer-controlled manipulation of collimator 38.

In another embodiment of the present invention, a confirmation image 102 is not prepared prior to delivery. In some cases, there is no time to prepare a confirmation image 102, or for other reasons, it is deemed unnecessary. In this situation, the radiation therapy is administered according to the dose distribution for planned treatment image 100, radiographic images (CT, MRI, x-ray etc.) taken simultaneously with or after the application of the prescribed radiation. After the radiation treatment is finished, the radiographic images are used in the same manner as the plurality of confirmation images 52 of the previous embodiment in the preparation of a fluence adjustment. If it appears that the region of interest or target has enlarged or changed significantly in shape, any underdosed voxels may be immediately dosed again while the patient is still in position so that they do not have to wait until the next appointment.

In yet another embodiment of the present invention, the fluence adjustment is computed during the application of the prescribed radiation. The x-rays or other radiographic projections detected by linear array detector 32 are used to detect shape/position changes to the region of interest 52 prior to delivery of radiation. The computer 40 analyzes the intensity pattern for a particular image slice and determines any necessary fluence adjustment in the same manner as described for the previous embodiments.

It is noted here that the examples shown in FIGS. 1 through 6 are by way of example only, and should not be used to limit the scope of the invention. In particular, the voxel grids shown in FIGS. 4–6 are rather course, simple approximations. Further, the indicated areas of treatment are in no way indicative of an actual course of radiation treatment for a given tumor, and any adjustments made may be isolated to the region at risk in some instances. The method of the present invention can also be used in veterinary applications.

Although the invention has been herein shown and described in what is perceived to be the most practical and preferred embodiments, it is to be understood that the invention is not intended to be limited to the specific embodiments set forth above. For example, different radiological equipment may be used to apply the radiation dose or obtain radiographic images. It is recognized that modifications may be made by one of skill in the art of the invention without departing from the spirit or intent of the invention and therefore, the invention is to be taken as including all reasonable equivalents to the subject matter of the appended claims.

We claim:

1. A method for modifying a prepared radiation treatment plan on-line in response to a detected change in the size, shape or position of a tumor in a patient comprising the steps of:

obtaining a first image of a tumorous region in a patient to be treated;

creating a treatment plan based on said first image;

placing the patient on a treatment table of a radiation therapy machine to receive a radiation treatment;

obtaining a second image of the tumorous region in the patient while the patient is on the treatment table receiving the radiation treatment;

modifying the treatment on-line based on changes in the tumorous region in the patient as represented in said second image.

2. A method of compensating for unexpected changes in any one of size, shape, or position of a tumor or sensitive structures in the delivery of radiation therapy comprising the steps of:

obtaining a first image of a patient, wherein said first image includes a visual representation of a tumor to be irradiated and sensitive structures to be avoided;

creating a treatment plan for irradiation of the tumor shown in said first image, the treatment plan comprising a voxel grid;

obtaining a second image of the patient while the patient is on a treatment table of a radiation therapy machine just prior to receiving radiation treatment, wherein said second image includes a visual representation of the tumor and the sensitive structures shown in said first image, and wherein the visual representation of any one of a size, shape, or position of any one of a tumor and sensitive structures is different from any one of the size, shape, or position of the visual representation of any one of the tumor and the sensitive structures in said first image; and without reoptimizing the treatment plan, at the time of treatment, manually adjusting the amount of radiation for select voxels in the voxel grid of the treatment plan to more accurately treat the tumor and mitigate damage to the sensitive structures, as shown in said second image.

3. The method of claim 2 wherein the step of manually adjusting the amount of radiation for select voxels in the voxel grid of the treatment plan is performed after a dose of radiation has been delivered to the patient in accordance with the treatment plan.

4. The method of claim 3 further comprising the step of delivering additional radiation to any underdosed voxels.

5. The method of claim 2 wherein the step of manually adjusting the amount of radiation for select voxels in the voxel grid of the treatment plan is performed just prior to delivery of a dose of radiation to the patient.

6. A method of compensating for unexpected changes in any one of size, shape, or position of a tumor or sensitive structures in the delivery of radiation therapy comprising the steps of:

obtaining a first image of a patient, wherein said first image includes a visual representation of a tumor to be irradiated and sensitive structures to be avoided;

creating a treatment plan for irradiation of the tumor shown in said first image, the treatment plan comprising a voxel grid;

obtaining a second image of the patient while the patient is on a treatment table of a radiation therapy machine just prior to receiving radiation treatment, wherein said second image includes a visual representation of the tumor and the sensitive structures shown in said first image, and wherein the visual representation of any one of a size, shape, or position of any one of a tumor and sensitive structures is different from any one of the size, shape, or position of the visual representation of any one of the tumor and the sensitive structures in said first image; and at the time of treatment, automatically adjusting the amount of radiation for select voxels in the voxel grid of the treatment plan to more accurately treat the tumor and mitigate damage to the sensitive structures, as shown in said second image.

7. The method of claim 6 wherein the step of automatically adjusting the amount of radiation for select voxels in the voxel grid of the treatment plan is performed after a dose of radiation has been delivered according to the treatment plan.

8. The method of claim 7 further comprising the step of delivering additional radiation to any underdosed voxels.

9. The method of claim 6 wherein the step of automatically adjusting the amount of radiation for select voxels in the voxel grid of the treatment plan is performed just prior to the delivery of radiation to the patient.

10. The method of claim 6 wherein the step of automatically adjusting the amount of radiation for select voxels in the voxel grid of the treatment plan is performed simultaneously with the delivery of radiation to the patient.

11. A method of adjusting a radiation treatment plan for treating a tumor of a patient to more closely conform the treatment plan to the size, shape, and position of the tumor or surrounding sensitive structure at the time of delivery of radiation therapy comprising the steps of:

positioning a patient on a treatment table of a radiation therapy machine to receive a dose of radiation in accordance with the treatment plan;

obtaining an image of the patient while the patient is on the treatment table;

modifying the treatment plan on-line based on changes in the tumor as represented in said image;

modifying the treatment plan on-line based on changes in the surrounding sensitive structure as represented in said image;

while the patient is still in position to receive the dose of radiation, increasing the radiation dose for any portion of the treatment plan that appears to be underdosed due to a change in the tumor, and decreasing the radiation dose for any portion of the treatment plan that appears to be overdosed due to a change in the tumor.

12. The method of claim 11 wherein each step of determining which portion of the treatment plan corresponds is performed manually.

13. The method of claim 12 wherein each steps of increasing the radiation dose and decreasing the radiation dose are performed manually.

14. The method of claim 11 wherein each step of determining which portion of the treatment plan corresponds is performed automatically.

15. The method of claim 14 wherein each steps of increasing the radiation dose and decreasing the radiation dose are performed automatically.

16. The method of claim 11 further comprising the step of delivering the radiation dose the patient after the step of increasing the radiation dose for any portion of the treatment plan that appears to be underdosed.

17. A method for radiation treatment comprising the steps of:

obtaining a first image of a tumorous region in a patient to be treated;

creating a treatment plan based on said first image;

placing the patient on a treatment table of a radiation therapy machine to receive a radiation treatment;

obtaining a second image of the tumorous region in the patient while the patient is on the treatment table being prepared to receive the radiation treatment;

modifying the treatment plan on-line based on changes in the tumorous region in the patient as represented in said second image; and treating the patient with the modified treatment plan.

* * * * *